United States Patent [19]

Schmolka

[11] Patent Number: 4,465,661

[45] Date of Patent: Aug. 14, 1984

[54] ORAL PRODUCT HAVING IMPROVED TASTE

[75] Inventor: Irving R. Schmolka, Grosse Ile, Mich.

[73] Assignee: BASF Wyandotte Corporation, Wyandotte, Mich.

[21] Appl. No.: 466,733

[22] Filed: Feb. 16, 1983

Related U.S. Application Data

[63] Continuation-in-part of Ser. No. 94,130, Nov. 14, 1979.

[51] Int. Cl.$^3$ .................... A61K 9/16; A61K 7/26
[52] U.S. Cl. ............................ 424/49; 426/651; 424/58
[58] Field of Search ............... 426/651; 424/49, 58

[56] References Cited

U.S. PATENT DOCUMENTS

| | | | |
|---|---|---|---|
| 2,422,145 | 6/1947 | Taylor | 426/651 |
| 2,435,744 | 2/1948 | Hartman | 426/651 |
| 2,508,978 | 5/1950 | Tribble | 426/651 |
| 2,677,700 | 5/1954 | Jackson | 424/49 |
| 2,773,801 | 12/1956 | Fox | 424/49 |
| 3,639,563 | 2/1972 | Januszewsky | 424/49 |
| 3,666,496 | 5/1972 | Honey et al. | 426/651 |
| 3,674,502 | 7/1972 | Honey et al. | 426/651 |
| 3,947,570 | 3/1976 | Pensak et al. | 424/49 |
| 4,130,638 | 12/1978 | Dhabhar et al. | 424/49 |
| 4,150,151 | 4/1979 | Pader et al. | 424/49 |

*Primary Examiner*—Shep K. Rose
*Attorney, Agent, or Firm*—Bernhard R. Swick

[57] ABSTRACT

Oral products such as mouthwashes and dentifrices are disclosed which utilize a polyoxyethylene derivative of a fatty alcohol having 15 to 20 carbon atoms wherein the polyoxyethylene chains are responsible for about 50 to about 90 percent of the molecular weight of the surfactant. Unexpectedly, the nonionic surfactants solubilize peppermint oil and other flavorants at ambient temperatures and below so that the mouthwash compositions of the invention remain clear and haze free. The visually clear dental creams of the invention also maintain their clarity at ambient temperatures and below. Both mouthwash and dental creams of the invention are free of the usual bitter surfactant taste.

4 Claims, No Drawings

ORAL PRODUCT HAVING IMPROVED TASTE

Cross Reference to Related Application

This application is a continuation-in-part of U.S. patent application, Ser. No. 94,130, filed Nov. 14, 1979.

BACKGROUND OF THE INVENTION

1. Field of the Invention

This invention relates to oral preparations including mouthwashes and dentifrices which are free from unpleasant, bitter surfactant taste and are stable, visually clear and haze free at ambient temperatures.

2. Description of the Prior Art

Tomlinson in U.S. Pat. No. 4,130,636 discloses dental creams and mouthwash compositions free from bitter surfactant taste wherein the surfactant is an alkyl polyglycol ether carboxylate. A mouthwash having superior taste characteristics and improved clarity is disclosed by Januszewski in U.S. Pat. No. 3,639,563. The improved clarity is obtained by selecting nonionic surface active agents for their ability to solubilize one or more oily components contained in the mouthwash. Thus, polyoxypropylene-polyoxyethylene block polymers and polyoxyethylene derivatives of sorbitan esters are disclosed as useful surfactants which solubilize certain oily components and thus provide improved clarity in the mouthwash.

Pensak et al, in U.S. Pat. No. 3,947,570, also disclose a visually clear, haze-free mouthwash free from unpleasant taste which includes a nonionic surfactant which is a polyoxyethylene derivative of a sorbitan ester. These references neither disclose nor suggest the applicant's use of a nonionic surfactant consisting of the polyoxyethylene derivative of a fatty alcohol having about 15 to about 20 carbon atoms and wherein the ethylene oxide derived component of the surfactant makes up about 50 to about 90 percent by weight of the surfactant.

Jackson et al, in U.S. Pat. No. 2,677,700, disclose polyoxyalkylene surface-active block polymers, Example 6 thereof disclosing a propoxylated cetyl alcohol. There is an indication, in column 24, that the surface-active agents disclosed would have freedom from the usual bitter taste generally associated with nonionic surfactants of the prior art. However, the surfactant compositions of Jackson et al are not those utilized by the applicant as components of a mouthwash or a dental cream.

SUMMARY OF THE INVENTION

An oral product can be prepared which is free of the usual bitter taste associated with most nonionic surfactants and yet has improved clarity at ambient temperatures and below by utilizing a particular nonionic surfactant solubilizing agent especially effective with peppermint flavoring oil. The nonionic surfactant selected for use in the inventive mouthwash and visually clear dental cream compositions of the invention is a polyoxyethylene derivative of a fatty alcohol containing about 15 to about 20 carbon atoms wherein the ethylene oxide derived component of said surfactant amounts to about 50 percent by weight to about 90 percent by weight of said surfactant composition. In addition to the advantages of using the polyoxyethylene surfactant in the oral products of the invention, as described above, the surfactants of the invention are biodegradable and thus contribute less to the pollution of the environment as compared to certain other types of polyoxyalkylene-based nonionic surfactants.

DETAILED DESCRIPTION OF THE INVENTION

In accordance with this invention, it has been found that mouthwash and dentifrice compositions can be prepared containing a tasteless polyoxyethylene fatty alcohol reaction product wherein the fatty alcohol contains about 15 to about 20 carbon atoms and wherein the ethylene oxide-derived portion of the surfactant is about 50 to about 90 percent by weight thereof. The use of said polyoxyethylene-fatty alcohol surfactant is particularly suited for use in a mouthwash wherein a water-insoluble flavoring oil such as peppermint oil is required to be solubilized so as to prevent cloudiness and haze formation at ambient temperatures and below.

Surprisingly, it has been found that the surfactants of the invention are tasteless and, therefore, additional formulation latitude is provided in the preparation of mouthwash compositions as well as dentifrice compositions. Thus, visually clear dentifrice compositions can be prepared containing a flavoring oil such as peppermint oil which retain clarity at ambient temperatures and below.

With a few exceptions, as noted in the discussion of prior art, generally all commercially available surfactants for use in oral products have a bitter taste. Heretofore, the bitter taste has been overcome by the use of a sweetening ingredient such as saccharin. As is well known, when saccharin is the sole sweetening agent, it too leaves a bitter taste and other sweeteners are often not acceptable because of the reluctance to add caries-inducing carbohydrate-based sweetening agents and because of storage stability problems. One object of the invention is the elimination of the problems in a mouthwash composition associated with solubilizing a flavoring oil, particularly peppermint oil, so as to avoid reduced clarity at ambient temperatures and below.

The invention is also directed to visually clear dentifrice compositions. Such compositions, when containing ordinarily water-insoluble flavoring oils such as peppermint oil, have reduced clarity where certain prior art nonionic surfactants are utilized in the dentifrice composition. In both types of oral products, the use of the nonionic surfactant of the invention alleviates problems related to overcoming the ordinarily bitter taste of prior art nonionic surfactants with sweetening agents.

Broadly, the instant invention provides for an oral product which is a visually clear dentifrice or a mouthwash having improved clarity at temperatures below ambient temperatures comprising a nonionic surfactant as described above. Generally, said nonionic surfactant is utilized in the visually clear dentifrice or the mouthwash of the invention as the sole surfactant component of the composition but it is also useful when blended with other conventional prior art surfactants in a major proportion of the mixture. Generally, about 0.1 to about 5.0 percent, preferably about 1 percent to about 3 percent, and most preferably, about 1 to about 2 percent, by weight of the nonionic surfactant of the invention is employed as the sole surfactant in either the visually clear dentifrice composition or the mouthwash composition of the invention. The water-insoluble flavoring oils utilized in the oral compositions of the invention, for instance peppermint oil, require a water solubilizing amount of the nonionic surfactant of the invention in order to effectually render the oral composition visually clear at ambient temperatures and below. Generally, where peppermint oil is employed in the composition, the weight ratio of said nonionic surfactant to said peppermint oil is greater than 1.5:1. Preferably, the ratio of said surfactant to peppermint oil is about 5:1 and most preferably 10:1.

Minor amounts of prior art nonionic surfactants can be employed in admixture with the nonionic surfactant of the invention without substantially contributing to reduction in clarity of the composition or resulting in the usual bitter taste associated with conventional prior art nonionic surfactants. Where mixtures of surfactants are used, generally about 10 to 20 percent by weight of conventional prior art nonionic surfactant is used with the surfactants of the invention. In addition, anionic or cationic organic surfactants can be employed in admixture with the nonionic surfactants of the invention.

Suitable anionic and cationic surfactants are water-soluble salts of higher fatty acids, monoglycerides of hydrogenated coconut oil fatty acids, higher alkyl sulfates such as sodium lauryl sulfate, alkylaryl sulfonates, such as sodium dodecylbenzene sulfonate, higher alkyl sulfoacetates, higher fatty acid esters of 1,2-dihydroxypropane sulfonates, olefin sulfonates and the substantially saturated higher aliphatic acylamides of lower aliphatic amino carboxylic compounds such as those having 12 to 16 carbon atoms in the fatty acid or acyl radicals and the like. Examples of useful substantially-saturated higher aliphatic acylamides of lower aliphatic amino carboxylic acids are N-lauroyl sarcosine and the sodium, potassium and ethanolamine salts of N-lauroyl, N-myristoyl, or N-palmitoyl sarcosine. These should be substantially free from soap or similar higher fatty acid materials which tend to substantially reduce the effectiveness of these compounds. The use of sarcosinate compounds particularly in dentifrice compositions is advantageous as is well known in the prior art since these materials exhibit a prolonged and marked effect in the inhibition of acid formation in the oral cavity as a consequence of carbohydrate breakdown.

Conventional nonionic surfactants suitable for use in admixture with the nonionic surfactant polyoxyalkylene-fatty alcohol surfactant of the invention include such nonionic surfactants as condensates of ethylene oxide with propylene oxide, condensates of propylene glycol and amphoteric agents such as quartenized imidazole derivatives. Additional examples of conventional nonionic surfactants suitable for use in minor amounts in the oral compositions of the invention are condensates of an alpha-olefin epoxide and a polyhydric alcohol containing 2 to about 10 carbon atoms and 2 to 6 hydroxyl groups with either ethylene oxide or a heteric mixture of ethylene oxide and propylene oxide. Such heteric polymers have a molecular weight in the range of 400 to 1600 and contain 40 to 80 percent by weight of ethylene oxide or a mixture of ethylene oxide and propylene oxide. The ratio of alpha-olefin epoxide to polyhydric alcohol is in a molar ratio of 1:1 to 1:3. The preparation of such conventional nonionic surfactants is well known in the prior art. Generally, such surfactants are manufactured under conditions of high temperature and high pressure. Generally, the nonionic surfactants are present in the proportion of about 0.1 to about 5 percent by weight.

Generally, the flavoring component is present as a denaturant in the non-toxic alcohol component, i.e., ethyl alcohol, utilized in a mouthwash composition. In the visually clear dentifrice compositions of the invention, such flavoring component must be added to the dentifrice mixture separately. The conventional flavoring components are exemplified by the following materials, menthol, anise oil, benzaldehyde, bitter almond oil, camphor, cedar leaf oil, chlorothymol, cinnamic aldehyde, cinnamon oil, citronella oil, clove oil, eucalyptol, lavendar oil, menthol, mustard oil, peppermint oil, phenyl salicylate, pine oil, pine needle oil, rosemary oil, sassafras oil, spearmint oil, thyme oil, thymol, and wintergreen oil.

The mouthwash compositions of the invention generally contain about 60 to 95 percent, preferably about 70 to 80 percent by weight of water and from 0 to about 25, preferably about 5 to about 20 percent by weight, most preferably about 15 percent by weight of a nontoxic alcohol such as isopropanol or ethanol. In addition to the flavoring component and the nonionic surfactant which is utilized as a solubilizing agent, the mouthwash compositions of the invention generally contain optional effective amounts of antibacterial agents such as quarternary ammonium compounds or the substantially saturated aliphatic acyl amides. Generally, these antibacterial agents are utilized in amounts of about 0.01 to about 0.1 percent by weight. The following illustrative antibacterial agents are useful: benzethonium chloride, diisobutylphenoxyethoxyethyldimethylbenzyl ammonium chloride, N-alkyl pyridinium chloride, N-cetyl pyridinium bromide, sodium N-lauroyl sarcosinate.

Additional adjuvants can be added to provide color, flavor, or sweetening effects, as desired. Examples of suitable sweetening agents include sucrose, lactose, maltose, sorbitol, sodium cyclamate, and saccharine. The coloring agent is typically added in an amount of 0.01 percent to about 0.02 percent by weight. Citric acid is often utilized as a flavor additive. All types of flavoring materials are generally used in amounts of about 0.01 to about 5.0 percent by weight, preferably about 0.05 percent to about 3.0 percent by weight.

Generally, a buffering ingredient is also added to the mouthwash compositions of the invention in order to prevent natural degradation of the flavoring components of the mouthwash. Generally, the pH of the mouthwash is adjusted to 3.5 to about 7, preferably from about 5 to about 6. The buffering ingredient such as an alkali metal salt of a weak organic acid, for instance, sodium benzoate, sodium citrate, sodium phosphate, or potassium tartrate is generally added in an amount of about 0.1 to about 1.0 percent by weight.

In addition to the water, nontoxic alcohol, nonionic surfactant and optional antibacterial, flavoring and pH buffereing ingredients, the mouthwash compositions of the invention can optionally contain at least one humectant selected from the group consisting of glycerine, sorbitol, and propylene glycol. Generally, such humectants are utilized in the proportion of about 8 percent to about 12 percent by weight based upon the total weight of the mouthwash composition. Preferably, the humectant is utilized in an amount of about 10 to 12 percent by weight.

The mouthwash compositions of the invention are prepared using methods similar to those well known in the art. Typically, the ingredients are combined in a specified amount in an amount of water sufficient to bring the total of components to 100 percent by weight. Preferably, the alcohol-soluble components are separately premixed in a suitable mixing vessel and subsequently added to the water. Those components having solubility in water are preferably added to the water before mixing the alcohol premixture into the water.

In the preparation of the visually clear, gelled dentifrice compositions of the invention, besides the inclusion of similar amounts of a flavoring component and a nonionic surfactant component, as described above, such compositions generally contain a humectant and a water-insoluble dental polishing agent. The humectant material is selected from the group consisting of at least one of glycerine, sorbital and propylene glycol and is present generally in an amount up to about 50 percent to about 80 percent of the visually clear dentifrice composition. Preferably, such compositions contain about 60 to 75 percent of humectant. Gelling agents are known in the prior art and can be selected from natural and synthetic gums such as gum tragacanth, methyl cellulose, polyvinyl pyrrolidone, and hydrophilic carboxyvinyl polymers such as those sold under the trademark Carbopol 934. Generally, about 0.5 percent to about 5 percent by weight of gelling agent is used. Often, thickening and gelling of the visually clear dentifrice can be accomplished by the addition of about 1 to about 5 percent by weight of a synthetic, finely-divided, pyrogenic silica such as those sold under the trademark CAB-O-SIL M5, SILOID 244, SILOID 266 and AEROSIL D-200. The proportion of flavoring oil is generally about 0.01 to about 5.0 percent, preferably about 0.05 to about 3 percent, by weight of the dentifrice composition and the proportion of nonionic surfactant is generally about 0.1 to about 5.0 percent by weight of said dentifrice composition. Generally, the proportion fo nonionic surfactant to flavoring oil, i.e., peppermint oil, is greater than 1.5:1, preferably at least 5:1 and most preferably about 10:1. The pH of the visually clear dentifrice composition of the invention can be adjusted to a pH of 3.5 to 7 or to the preferred pH range of about 5 to about 6 utilizing buffering materials as disclosed above and by the use fo acids such as citric, acetic, chloropropionic, malonic, formic, fumaric, methoxyacetic, and the water-soluble alkali metal salts thereof. Because the nonionic surfactant utilized in the visually clear dentifrice compositions of the invention is free of bitter taste, it is often unnecessary to utilize sweetening materials. Thus, greater formulating freedom is obtained and the flavoring and sweetening materials utilized are not undesirably changed in their effectiveness over the characteristics of the pure flavoring or sweetening materials.

Since the usual water-insoluble polishing agents of the type commonly employed in prior art dental creams would tend to reduce the visual clarity of the dentifrice, ordinarily rendering the dentifrice opaque, when visually clear dentifrice compositions are required a dental polishing agent is selected from those polishing agents which have refractive indices close to the refractive indices of the remainder of the dentifrice composition. Generally, the polishing agent is utilized in amounts of about 5 to about 50 percent, preferably about 5 to about 15 percent, by weight of the total weight of the visually clear dentifrice. Examples of suitable polishing agents are certain colloidal silicas and silicates, for instance, those silicas sold under the trademark SILOID 72 or under the trademark SANTOCEL 100 and certain synthetic alkali metal aluminosilicate complexes such as sodium alumina silicate.

Various other adjuvants are often employed in dentifrice formulations such as coloring agents, preservatives, silicone compounds, chlorophyll compounds, ammoniated materials such as urea, diammonium phosphate and mixtures thereof and other conventional components. These adjuvants are incorporated in the instant visually clear dentifrice compositions in amounts which do not substantially adversely effect the visual clarity of the dentifrice compositions. Additional optional ingredients include antibacterial agents as recited above.

The following examples more fully describe the oral products of the invention and show the unexpected results obtained by the use of the nonionic surfactants disclosed herein. The examples are intended for the purpose of illustration and are not to be construed as limiting in any way. Unless otherwise indicated, all parts, percentages and proportions are by weight and all temperatures are in degrees centigrade.

EXAMPLE 1

A mouthwash of the invention was prepared by blending peppermint oil into an aqueous 95 percent ethyl alcohol solution. Glycerine, sodium saccharin, sodium citrate are dissolved in water together with the surfactant of the invention. The alcohol aqueous solutions are blended and the mixture is bottled and the appearance noted. A clear solution is obtained which, upon cooling to a temperature of 2° C., is either clear or, at most, faintly opalescent. The composition of the mouthwash is as follows:

| Ingredient | Parts by Weight |
| --- | --- |
| 95% ethyl alcohol | 15.0 |
| oil of peppermint | 0.25 |
| water | 72.00 |
| sodium saccharin | 0.05 |
| sodium citrate | 1.7 |
| glycerine | 10.0 |
| $C_{15}$ fatty alcohol ethoxylated so as to contain 60% polymerized ethylene oxide residue | 1.0 |

EXAMPLES 2–6

Example 1 is repeated substituting the following nonionic surfactants for the surfactant utilized in Example 1.

A fatty alcohol ethoxylate wherein the fatty alcohol is a mixture of alcohols having 16 to 18 carbon atoms ethoxylated so as to contain 80 percent by weight of the total weight of the nonionic surfactant of the residue of ethylene oxide, A 16 carbon chain fatty alcohol ethoxylated so as to contain 62 percent polymerized ethylene oxide residue, A 16 carbon chain fatty alcohol ethoxylated so as to contain 78 percent polymerized ethylene oxide residue, A 20 carbon chain fatty alcohol ethoxylated so as to contain 55 percent polymerized ethylene oxide residue, A 15 carbon chain fatty alcohol ethoxylated so as to contain 90 percent polymerized ethylene oxide residue, In each mouthwash formulation prepared, a clear solution is obtained which, upon cooling to 2° C., either remains clear or, at most, becomes faintly opalescent.

EXAMPLE 7

A mouthwash of the invention was prepared by blending peppermint oil into an aqueous 95 percent ethyl alcohol solution. Glycerine, sodium saccharin, and sodium citrate solution are dissolved in water together with the surfactant of the invention. The alcohol and aqueous solutions are blended and the mixture bottled and the appearance noted. The composition of the mouthwash was as follows:

| Ingredient | Parts by Weight |
| --- | --- |
| 95% ethyl alcohol | 15.0 |
| oil of peppermint | 0.25 |
| sodium saccharin | 0.05 |
| sodium citrate solution* | 73.7 |
| glycerine | 10.0 |
| $C_{15}$ fatty alcohol ethoxylated so as to contain 68% polymerized ethylene oxide residue | 1.0 |

*Prepared by dissolving by weight 19.2 parts of citric acid and 8 parts sodium hydroxide in 200 parts of water.

EXAMPLES 8–13

(Comparative)

Example 7 was repeated substituting the following nonionic surfactants for the surfactant utilized in Example 1.

(8) A fatty alcohol ethoxylate wherein the fatty alcohol is a mixture of alcohols having 12 to 15 carbon atoms ethoxylated so as to contain 66 percent by weight of the total weight of the nonionic surfactant of the residue of polymerized ethylene oxide, (9) A 16 carbon chain fatty alcohol propoxylated so as to contain 69.4 percent of polymerized propylene oxide residue,

(10) A 14 carbon chain fatty alcohol ethoxylated so as to contain 62 percent polymerized ethylene oxide residue,

(11) A 14 carbon chain fatty alcohol ethoxylated so as to contain 67.1 percent polymerized ethylene oxide residue,

(12) A 12 carbon chain fatty alcohol ethoxylated so as to contain 63.8 percent polymerized ethylene oxide residue,

(13) Polysorbate 80 sorbitan monooleate ethoxylate a surfactant well known to those skilled in the art.

EXAMPLE 14

A mouthwash of the invention was prepared by blending peppermint oil into 95 percent aqueous ethyl alcohol. Glycerine was dissolved in water together with the surfactant of the invention. The alcohol aqueous solutions are blended and the mixture is bottled and the appearance noted. The composition of the mouthwash was as follows:

| Ingredient | Parts by Weight |
| --- | --- |
| 95% ethyl alcohol | 10.0 |
| oil of peppermint | 2.0 |
| water | 75.00 |
| glycerine | 10.0 |
| $C_{15}$ fatty alcohol ethoxylated so as to contain 68% polymerized ethylene oxide residue | 3.0 |

EXAMPLES 15–16

(Comparative)

Example 14 was repeated substituting the following nonionic surfactants for the surfactant utilized in Example 14.

(15) A fatty alcohol ethoxylate wherein the fatty alcohol is a mixture of alcohols having 12 to 15 carbon atoms ethoxylated so as to contain 60 percent by weight of the total weight of the nonionic surfactant of the residue of polymerized ethylene oxide,

(16) Cetyl alcohol propoxylated so as to contain 69.4 percent by weight of polymerized propylene oxide residue.

Each mouthwash formulation prepared was observed for clarity and those which were clear were tasted. Those that were not clear were not tasted since they failed to meet the objectives of the instant invention and, therefore, did not require further testing.

The taste test consisted of pouring about 5 milliliters of the mouthwash from its container into a beaker. The contents were then transferred to the taster's mouth and swirled around therein followed by ejection. This was followed by a five minute rinse with cold water to remove the taste of the previous sample. The results of the clarity and taste tests were as follows:

| Example | Source | Results |
| --- | --- | --- |
| 7 | Invention | Clear - sweet, mild taste |
| 8 | Comparative | Clear - bitter, unpleasant taste |
| 9 | Comparative (Ex. 6 U.S. 2,677,700) | Not clear - insoluble layer on surface |
| 10 | Comparative | Clear - initial good taste but bitter aftertaste |
| 11 | Comparative | Clear - initial good taste but bitter aftertaste |
| 12 | Comparative | Clear - strong, bitter flavor |
| 13 | Comparative | Clear - strong, bitter flavor |
| 14 | Invention | Clear - mild, slightly sweet |
| 15 | Comparative | Clear - strong, unpleasant taste |
| 16 | Comparative (Ex. 6 U.S. 2,677,700) | Not clear - two layer system |

From the above table it can be seen that only the composition according to the instant invention produces an aqueous mouthwash which is both free from unpleasant, bitter surfactant taste and is stable, visually clear and haze free.

EXAMPLE 17

The following visually clear dentifrice is prepared:

| Ingredient | Parts by Weight |
| --- | --- |
| Sorbitol (70%) | 75.0 |
| Glycerine | 15.1 |
| Silicated clay | 2.0 |
| AEROSIL D-200 | 5.0 |
| Sodium alumina silicate | 16.0 |
| Oil of peppermint | 1.0 |
| Coloring agent | 1.0 |
| Water | 20.0 |
| $C_{15}$ fatty alcohol ethoxylate containing 60 percent by weight polymerized ethylene oxide residue | 2.0 |

It is noted that the sodium alumina silicate employed in this example is a complex having a refractive index of 1.46, a moisture content of about 6 percent and an average particle size of about 35 microns.

While this invention has been described with reference to certain specific embodiments, it will be recognized by those skilled in the art that many variations are possible without departing from the scope and spirit of the invention and it will be understood that it is intended to cover all changes and modifications of the invention disclosed herein for the purpose of illustration which do not constitute departures from the spirit and scope of the invention.

The embodiments of the invention in which an exclusive property of privilege is claimed are as follows:

1. An aqueous mouthwash free from unpleasant, bitter surfactant taste which is stable, visually clear, and haze free at ambient temperatures consisting essentially of about 60 to about 95 percent by weight of water, about 0.05 to about 3.0 percent by weight of peppermint oil, about 0.1 to about 5.0 percent by weight of a nonionic surfactant consisting essentially of a polyoxyethylene derivative of the fatty alcohol having about 15 to about 20 carbon atoms wherein about 50 to about 90 percent by weight of said nonionic surfactant is derived from ethylene oxide and from about 5 to about 20 percent by weight of ethanol or isopropanol and the weight ratio of said nonionic surfactant to said peppermint oil is greater than 1.5:1.

2. A mouthwash according to claim 1 wherein the weight ratio of said surfactant to said peppermint oil is about 10:1.

3. A mouthwash according to claim 1 further including a humectant selected from the group consisting of glycerine, sorbitol and propylene glycol in an amount up to about 12 percent by weight.

4. The mouthwash of claim 3 including glycerine in an amount of about 10 percent by weight.

* * * * *